United States Patent
Mallo et al.

(10) Patent No.: US 9,138,703 B2
(45) Date of Patent: *Sep. 22, 2015

(54) COMPOSITION MADE OF POLYALKOXYLATED DERIVATIVES OF TRIMETHYLOLPROPANE AND FATTY ALCOHOLS, METHOD FOR PREPARING SAID COMPOSITION, AND USE THEREOF AS A REVERSER IN SELF-REVERSIBLE REVERSE LATEXES

(71) Applicant: SOCIETE D'EXPLOITATION DE PRODUITS POUR LES INDUSTRIES CHIMIQUES SEPPIC, Paris (FR)

(72) Inventors: Paul Mallo, Croissy-sur-Seine (FR); Herve Rolland, Castres (FR); Georges Da Costa, Saix (FR); Olivier Braun, Castres (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/211,347

(22) Filed: Mar. 14, 2014

(65) Prior Publication Data
US 2014/0213705 A1    Jul. 31, 2014

Related U.S. Application Data

(62) Division of application No. 13/696,311, filed as application No. PCT/FR2011/050817 on Apr. 11, 2011, now Pat. No. 8,846,769.

(30) Foreign Application Priority Data

May 6, 2010   (FR) ...................... 10 53532

(51) Int. Cl.
| | | |
|---|---|---|
| B01F 17/00 | (2006.01) |
| C07C 41/01 | (2006.01) |
| C08K 5/05 | (2006.01) |
| C08K 5/06 | (2006.01) |
| C07C 43/13 | (2006.01) |
| C08F 2/32 | (2006.01) |
| C08K 5/1525 | (2006.01) |
| C08F 220/06 | (2006.01) |
| C08F 220/58 | (2006.01) |

(52) U.S. Cl.
CPC ......... *B01F 17/0021* (2013.01); *B01F 17/0028* (2013.01); *C07C 41/01* (2013.01); *C07C 43/135* (2013.01); *C08F 2/32* (2013.01); *C08K 5/05* (2013.01); *C08K 5/06* (2013.01); *C08K 5/1525* (2013.01); *C08F 220/06* (2013.01); *C08F 2220/585* (2013.01)

(58) Field of Classification Search
None
See application file for complete search history.

(56) References Cited

U.S. PATENT DOCUMENTS

| 4,374,282 A * | 2/1983 | Maldonado et al. ......... 568/672 |
| 2005/0131205 A1 | 6/2005 | Hggman et al. |
| 2008/0312343 A1 | 12/2008 | Braun et al. |
| 2012/0157552 A1 | 6/2012 | Braun et al. |

FOREIGN PATENT DOCUMENTS

| EP | 0 161 038 | 11/1985 |
| FR | 2 467 186 | 4/1981 |
| FR | 2 879 607 | 6/2006 |
| GB | 1 482 515 | 8/1977 |

OTHER PUBLICATIONS

Xiaofen, et al.; "Construction of Multifunctional Coatings Via Layer-by-Layer Assembly of Sulfonated Hyperbranched Polyether and Chitosan"; vol. 26, No. 4; Sep. 18, 2009; pp. 2624-2629.

* cited by examiner

*Primary Examiner* — Michael B Pallay
(74) *Attorney, Agent, or Firm* — Young & Thompson

(57) ABSTRACT

A novel composition made of polyalkoxylated derivatives of trimethylolpropane and fatty alcohols, the preparation thereof and the use thereof as a reversing agent for a reversible reverse latex.

10 Claims, No Drawings

COMPOSITION MADE OF POLYALKOXYLATED DERIVATIVES OF TRIMETHYLOLPROPANE AND FATTY ALCOHOLS, METHOD FOR PREPARING SAID COMPOSITION, AND USE THEREOF AS A REVERSER IN SELF-REVERSIBLE REVERSE LATEXES

FIELD OF THE INVENTION

The present patent application relates to the use of compounds derived from trimethylolpropane oxetane as inverters in self-invertible inverse latexes.

BACKGROUND OF THE INVENTION

Inverse latexes of polyelectrolytes based on partially or completely salified 2-methyl-2-[(1-oxo-2-propenyl)amino]-1-propanesulfonic acid (also known as 2-acrylamido-2-methylpropanesulfonic acid, ATBS or AMPS), and their use in cosmetics and/or in pharmaceuticals have formed the subject matter of numerous patent applications. However, the presence of significant amounts of water and oil in these inverse latexes represents a not insignificant disadvantage in terms of volume, of cost and sometimes of increased risks and/or of toxic effects.

Solutions have thus been developed for increasing the concentration of polyelectrolytes in the final inverse latexes, for example by subjecting the reaction medium, at the end of polymerization, to a vacuum distillation stage in order to remove a more or less large portion of water and oil. However, this distillation is problematic to carry out as it often brings about a destabilization of the inverse latex which is necessary to counter by the prior addition of stabilizing agents. European patent applications EP 0 161 038 and EP 0 126 528 and British patent application GB 1 482 515 disclose such a use of stabilizing polymers.

The disadvantage of these stabilizing products is that they comprise alcohols or glycols which can cause environmental problems. Furthermore, sometimes the reaction medium sets solid during the distillation stage, without this phenomenon ever having been truly explained, but the certain consequence of which is the destruction of the batch of inverse latex in the course of preparation and difficult and expensive cleaning of the reactor used. Finally, even if the distillation takes place correctly, the inverse latexes obtained often invert with difficulty when they are employed in an aqueous phase and they also exhibit a high viscosity and sometimes microgels within them. These disadvantages thus prohibit their use in the manufacture of cosmetic formulations and/or of textile printing pastes. In order to overcome these disadvantages, the inventors have developed an inverse latex disclosed in the French patent application published under the number FR 2 879 607 comprising from 50% to 80% by weight of a polyelectrolyte comprising from 0.01 mol % to 10 mol % of at least one monomer unit derived from the compound of formula (A):

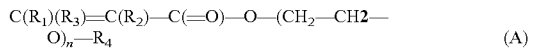

(A)

in which the $R_1$, $R_2$ and $R_3$ radicals, which are identical or different, represent, independently of one another, a halogen atom or a linear or branched alkyl radical comprising from 1 to 4 carbon atoms, the $R_4$ radical represents a saturated or unsaturated and linear or branched aliphatic radical comprising from 6 to 30 carbon atoms and n represents a number between 1 and 50.

However, when this composition is used to prepare a thickened formulation, the rate of inversion of the inverse latex in the aqueous phase, that is to say the time necessary to obtain the maximum development of the viscosity, remains fairly low, which means, for the user, a loss of time during the use of this product, in particular in the industrial phase for preparing cosmetic formulations and/or textile printing pastes. This is because it is well known that the inversion time for inverse latexes increases very considerably as a function of the scale of use. Furthermore, the stability over time of the inverse latexes described in FR 2 879 607 is not completely satisfactory. This is because a fairly rapid phenomenon of release of oil at the surface is observed during storage.

The inventors have thus sought to develop inverse latexes which do not exhibit the abovementioned disadvantages.

SUMMARY OF THE INVENTION

According to a first aspect, the subject matter of the invention is a surfactant composition (C) which comprises, per 100 mol %:

1)—a proportion of greater than or equal to 10 mol % and of less than or equal to 50 mol % of a composition $(C_{II})$ comprising, per 100 mol %:

α)—from 60 mol % to 100 mol % of a compound of formula (II):

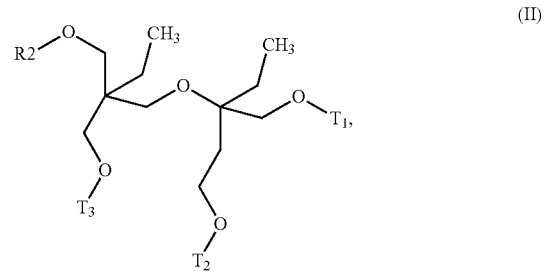

(II)

in which:

R2 represents a linear or branched alkyl radical comprising 12 carbon atoms, $T_1$ represents a hydrogen atom or a (—$CH_2$—$CH_2$—O—)$_{m1}$—H radical in which m1 is an integer of greater than or equal to zero and less than or equal to ten, $T_2$, which is identical to or different from $T_1$, represents a hydrogen atom or a (—$CH_2$—$CH_2$—O—)$_{m2}$—H radical in which m2 is an integer of greater than or equal to zero and less than or equal to ten, and $T_3$, which is identical to or different from $T_1$ and $T_2$, represents a hydrogen atom or a (—$CH_2$—$CH_2$—O—)$_{m3}$—H radical in which m3 is an integer of greater than or equal to zero and less than or equal to ten, it being understood that the sum m1+m2+m3 is greater than 0 and less than or equal to ten;

β)—optionally up to 40 mol % of a compound of formula (II'):

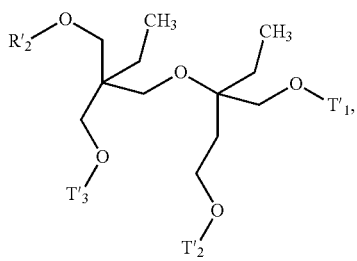

(II')

in which:
- R'$_2$ represents a linear or branched alkyl radical comprising 14 carbon atoms,
- T'$_1$ represents a hydrogen atom or a (—CH$_2$—CH$_2$—O—)$_{m1}$—H radical in which m1 is an integer of greater than or equal to zero and less than or equal to ten,
- T'$_2$, which is identical to or different from T'$_1$, represents a hydrogen atom or a (—CH$_2$—CH$_2$—O—)$_{m2}$—H radical in which m2 is an integer of greater than or equal to zero and less than or equal to ten, and
- T'$_3$, which is identical to or different from T'$_1$ and T'$_2$, represents a hydrogen atom or a (—CH$_2$—CH$_2$—O—)$_{m3}$—H radical in which m3 is an integer of greater than or equal to zero and less than or equal to ten,
- it being understood that the sum m1+m2+m3 is greater than 0 and less than or equal to ten; and
- γ)—optionally up to 10 mol % of a compound of formula (II''):

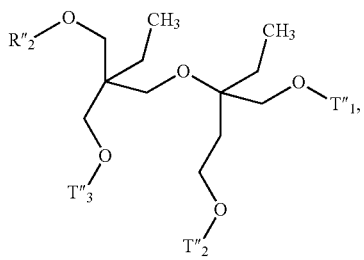

(II'')

in which:
- R''$_2$ represents a linear or branched alkyl radical comprising 16 carbon atoms,
- T''$_1$ represents a hydrogen atom or a (—CH$_2$—CH$_2$—O—)$_{m1}$—H radical in which m1 is an integer of greater than or equal to zero and less than or equal to ten,
- T''$_2$, which is identical to or different from T''$_1$, represents a hydrogen atom or a (—CH$_2$—CH$_2$—O—)$_{m2}$—H radical in which m2 is an integer of greater than or equal to zero and less than or equal to ten, and
- T''$_3$, which is identical to or different from T''$_1$ and T''$_2$, represents a hydrogen atom or a (—CH$_2$—CH$_2$—O—)$_{m3}$—H radical in which m3 is an integer of greater than or equal to zero and less than or equal to ten,
- it being understood that the sum m1+m2+m3 is greater than 0 and less than or equal to ten;

2)—a proportion of greater than or equal to 50 mol % and of less than or equal to 90 mol % of a composition (C$_{III}$) comprising, per 100 mol %:
- α)—from 60 mol % to 100 mol % of a compound of formula (III):

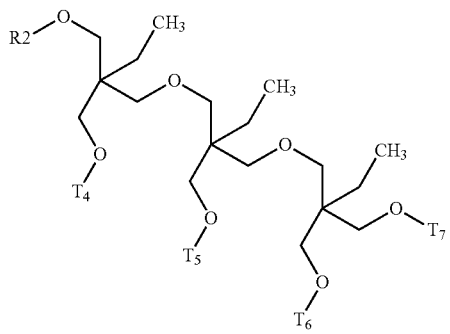

(III)

or of its isomer of formula (IV):

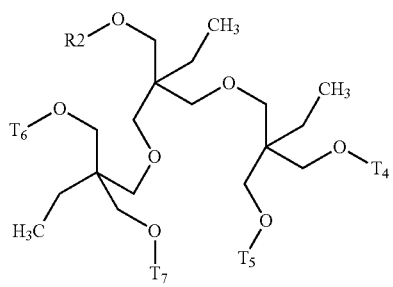

(IV)

or of the mixture of these two isomers,
in which formulae (III) and (IV):
- R2 represents a linear or branched alkyl radical comprising 12 carbon atoms,
- T$_4$ represents a hydrogen atom or a (—CH$_2$—CH$_2$—O—)$_{m4}$—H radical in which m4 is an integer of greater than or equal to zero and less than or equal to ten,
- T$_5$, which is identical to or different from T$_4$, represents a hydrogen atom or a (—CH$_2$—CH$_2$—O—)$_{m5}$—H radical in which m5 is an integer of greater than or equal to zero and less than or equal to ten,
- T$_6$, which is identical to or different from T$_4$ and T$_5$, represents a hydrogen atom or a (—CH$_2$—CH$_2$—O—)$_{m6}$—H radical in which m6 is an integer of greater than or equal to zero and less than or equal to ten,
- T$_7$, which is identical to or different from T$_4$, T$_5$ and T$_6$, represents a hydrogen atom or a (—CH$_2$—CH$_2$—O—)$_{m7}$—H radical in which m7 is an integer of greater than or equal to zero and less than or equal to ten,
- it being understood that the sum m4+m5+m6+m7 is greater than 0 and less than or equal to ten;
- β)—optionally up to 40 mol % of a compound of formula (III'):

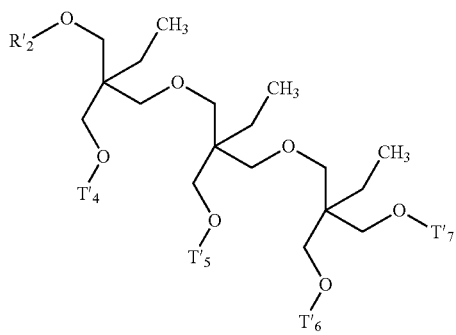

(III')

or of its isomer of formula (IV'):

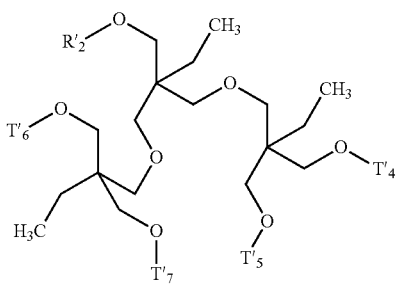
(IV')

or of the mixture of these two isomers,
in which formulae (III') and (IV'):
- $R'_2$ represents a linear or branched alkyl radical comprising 14 carbon atoms,
- $T'_4$ represents a hydrogen atom or a (—$CH_2$—$CH_2$—O—)$_{m4}$—H radical in which m4 is an integer of greater than or equal to zero and less than or equal to ten,
- $T'_5$, which is identical to or different from $T'_4$, represents a hydrogen atom or a (—$CH_2$—$CH_2$—O—)$_{m5}$—H radical in which m5 is an integer of greater than or equal to zero and less than or equal to ten,
- $T'_6$, which is identical to or different from $T'_4$ and $T'_5$, represents a hydrogen atom or a (—$CH_2$—$CH_2$—O—)$_{m6}$—H radical in which m6 is an integer of greater than or equal to zero and less than or equal to ten, and
- $T'_7$, which is identical to or different from $T'_4$, $T'_5$ and $T'_6$, represents a hydrogen atom or a (—$CH_2$—$CH_2$—O—)$_{m7}$—H radical in which m7 is an integer of greater than or equal to zero and less than or equal to ten,
- it being understood that the sum m4+m5+m6+m7 is greater than 0 and less than or equal to ten; and γ)—optionally up to 10 mol % of a compound of formula (III"):

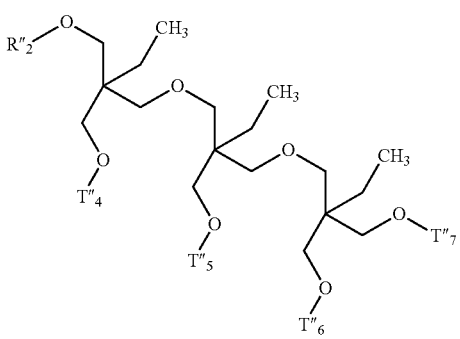
(III")

or of its isomer of formula (IV"):

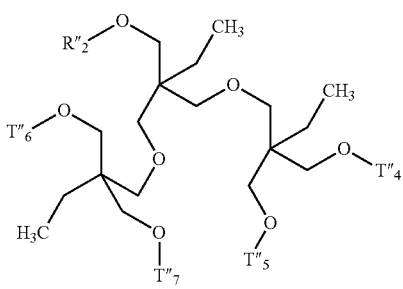
(IV")

or of the mixture of these two isomers,
in which formulae (III") and (IV"):
- $R''_2$ represents a linear or branched alkyl radical comprising 16 carbon atoms,
- $T''_4$ represents a hydrogen atom or a (—$CH_2$—$CH_2$—O—)$_{m4}$—H radical in which m4 is an integer of greater than or equal to zero and less than or equal to ten,
- $T''_5$, which is identical to or different from $T''_4$, represents a hydrogen atom or a (—$CH_2$—$CH_2$—O—)$_{m5}$—H radical in which m5 is an integer of greater than or equal to zero and less than or equal to ten,
- $T''_6$, which is identical to or different from $T''_4$ and $T''_5$, represents a hydrogen atom or a (—$CH_2$—$CH_2$—O—)$_{m6}$—H radical in which m6 is an integer of greater than or equal to zero and less than or equal to ten, and
- $T''_7$, which is identical to or different from $T''_4$, $T''_5$ and $T''_6$, represents a hydrogen atom or a (—$CH_2$—$CH_2$—O—)$_{m7}$—H radical in which m7 is an integer of greater than or equal to zero and less than or equal to ten,
- it being understood that the sum m4+m5+m6+m7 is greater than 0 and less than or equal to ten.

According to another specific aspect of the present invention, said surfactant composition (C) as defined above additionally comprises:

3)—up to 5 mol % of a composition ($C_γ$) comprising, per 100 mol %:
α)—from 60 mol % to 100 mol % of a compound of formula (V):

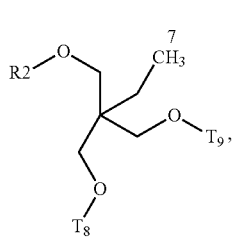
(V)

in which:
- R2 represents a linear or branched alkyl radical comprising 12 carbon atoms,
- $T_8$ represents a hydrogen atom or a (—$CH_2$—$CH_2$—O—)$_{m8}$—H radical in which m8 is an integer of greater than or equal to zero and less than or equal to ten,
- $T_9$, which is identical to or different from $T_8$, represents a hydrogen atom or a (—$CH_2$—$CH_2$—O—)$_{m9}$—H radical in which m9 is an integer of greater than or equal to zero and less than or equal to ten, and
- it being understood that the sum m8+m9 is greater than 0 and less than or equal to ten;

β)—optionally up to 40 mol % of a compound of formula (V'):

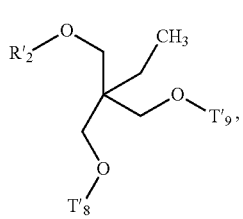
(V')

in which:
R'$_2$ represents a linear or branched alkyl radical comprising 14 carbon atoms,
T'$_8$ represents a hydrogen atom or a (—CH$_2$—CH$_2$—O—)$_{m8}$—H radical in which m8 is an integer of greater than or equal to zero and less than or equal to ten,
T'$_9$, which is identical to or different from T'$_8$, represents a hydrogen atom or a (—CH$_2$—CH$_2$—O—)$_{m9}$—H radical in which m9 is an integer of greater than or equal to zero and less than or equal to ten, and
it being understood that the sum m8+m9 is greater than 0 and less than or equal to ten; and
γ)—optionally up to 10 mol % of a compound of formula (V"):

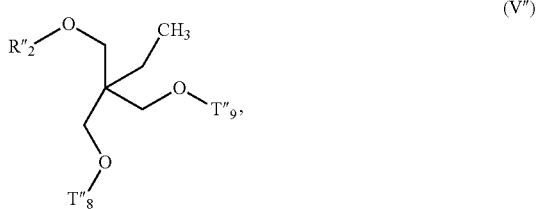

in which:
R"$_2$ represents a linear or branched alkyl radical comprising 16 carbon atoms,
T"$_8$ represents a hydrogen atom or a (—CH$_2$—CH$_2$—O—)$_{m8}$—H radical in which m8 is an integer of greater than or equal to zero and less than or equal to ten,
T"$_9$, which is identical to or different from T"$_8$, represents a hydrogen atom or a (—CH$_2$—CH$_2$—O—)$_{m9}$—H radical in which m9 is an integer of greater than or equal to zero and less than or equal to ten, and
it being understood that the sum m8+m9 is greater than 0 and less than or equal to ten.

According to another specific aspect of the present invention, said active composition (C) as defined above additionally comprises:
4)—up to 5 mol % of a composition (C$_{VI}$) comprising, per 100 mol %:
α)—from 60 mol % to 100 mol % of a compound of formula (VI):

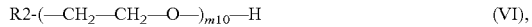
R2-(—CH$_2$—CH$_2$—O—)$_{m10}$—H (VI), in which R2 represents a linear or branched alkyl radical comprising 12 carbon atoms and m10 is an integer of greater than or equal to zero and less than or equal to ten;
β)—optionally up to 40 mol % of a compound of formula (VI'):

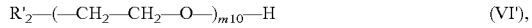
R'$_2$—(—CH$_2$—CH$_2$—O—)$_{m10}$—H (VI'), in which R'$_2$ represents a linear or branched alkyl radical comprising 14 carbon atoms and m10 is an integer of greater than or equal to zero and less than or equal to ten; and
γ)—optionally up to 10 mol % of a compound of formula (VI"):

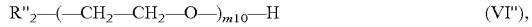
R"$_2$—(—CH$_2$—CH$_2$—O—)$_{m10}$—H (VI"), in which R"$_2$ represents a linear or branched alkyl radical comprising 16 carbon atoms and m10 is an integer of greater than or equal to zero and less than or equal to ten.
According to a specific aspect of the present invention, said surfactant composition (C) as defined above comprises:

1)—a proportion of greater than or equal to 20 mol % and of less than or equal to 50 mol % of a composition (C$_{II}$) as defined above;
2)—a proportion of greater than or equal to 50 mol % and of less than or equal to 80 mol % of a composition (C$_{III}$) as defined above.

According to another specific aspect of the present invention:
1)—said composition (C$_{II}$) comprises, per 100 mol %:
α)—from 60 mol % to 80 mol % of the compound of formula (II),
β)—from 15 mol % to 30 mol % of the compound of formula (II'), and
γ)—up to 10 mol % of the compound of formula (II"), and
2)—said composition (C$_{III}$) comprises, per 100 mol %:
α)—from 60 mol % to 80 mol % of the compound of formula (III), of its isomer of formula (IV) or of the mixture of these isomers,
β)—from 15 mol % to 30 mol % of the compound of formula (III'), of its isomer of formula (IV') or of the mixture of these isomers, and
γ)—up to 10 mol % of the compound of formula (III"), of its isomer of formula (IV") or of the mixture of these isomers.

Another subject matter of the invention is a process for the preparation of said surfactant composition (C) as defined above, characterized in that it comprises the following successive stages:
a stage a) of reaction of a mixture of alcohols comprising, per 100 mol %:
from 60 mol % to 100 mol % of a compound of formula (VII),

R2—O—H (VII), in which R2 represents a linear or branched alkyl radical comprising 12 carbon atoms;
optionally up to 40 mol % of a compound of formula (VII'):

R'$_2$—O—H (VII'), in which R'$_2$ represents a linear or branched alkyl radical comprising 14 carbon atoms, and
optionally up to 10 mol % of a compound of formula (VI"):

R"$_2$—O—H (VII"), in which R"$_2$ represents a linear or branched alkyl radical comprising 16 carbon atoms;
with a stoichiometric excess of 3-(hydroxymethyl)-3-ethyloxetane of formula (VIII):

in order to form a composition (C') comprising the compound of formula (IX):

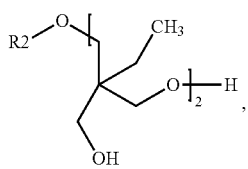
(IX)

in which R2 is as defined above;
optionally the compound of formula (IX'):

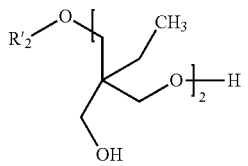
(IX')

in which R'$_2$ is as defined above;
optionally the compound of formula (IX"):

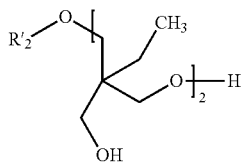
(IX")

in which R"$_2$ is as defined above;
the compound of formula (X):

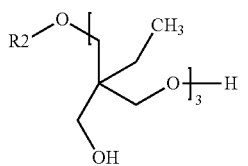
(X)

or its isomer of formula (XI):

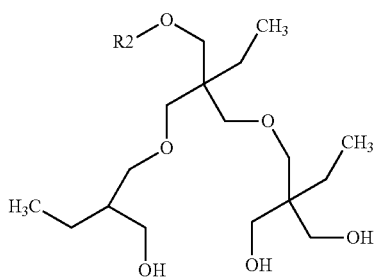
(XI)

or a mixture of these two isomers;
in which compounds of formulae (X) and (XI) R2 is as defined above;
optionally the compound of formula (X'):

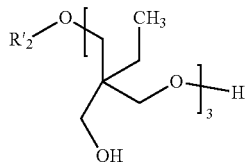
(X')

or its isomer of formula (XI'):

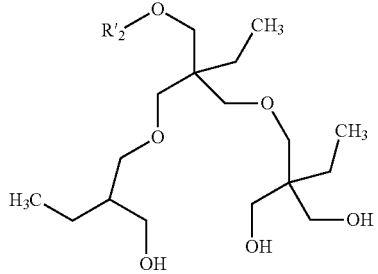
(XI')

or a mixture of these two isomers;
in which compounds of formulae (X') and (XI') R'$_2$ is as defined above;
optionally the compound of formula (X"):

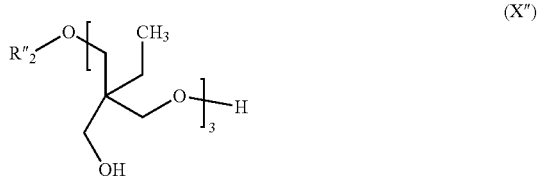
(X")

or its isomer of formula (XI"):

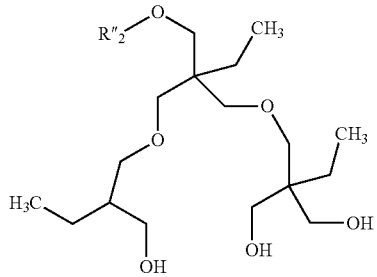
(XI")

or a mixture of these two isomers;
in which compounds of formulae (X") and (XI") R"$_2$ is as defined above;
a stage b) of reaction, in the desired stoichiometric ratio, of said composition (C') with ethylene oxide of formula (XII):

(XII)

in order to form said surfactant composition (C).

Another subject matter of the invention is the intermediate composition C' of the process as defined above.

Another subject matter of the invention is the intermediate compounds of formulae (IX), (X) and (XI) of the process as defined above.

A final subject matter of the invention is the use of the surfactant composition (C) as defined above as emulsifying agent of oil-in-water (O/W) type and more particularly as emulsifying agent of oil-in-water (O/W) type, more particularly as inverting agent for a self-invertible inverse latex, alone or as a mixture with other emulsifying agents capable of preparing and intended to prepare an emulsifying system ($S_2$) of oil-in-water (O/W) type.

DETAILED DESCRIPTION OF THE INVENTION

The term "self-invertible inverse latex" denotes a water-in-oil emulsion of a crosslinked polymer, obtained by inverse emulsion polymerization of the monomers employed, said water-in-oil emulsion of a polymer being capable, by virtue of the presence within it of an emulsifying system ($S_2$) of oil-in-water (O/W) type, said inverting agent, of inverting to give an oil-in-water emulsion by simple dispersion in water with slow mechanical stirring, thus bringing about the thickening of this aqueous phase.

An example of a self-invertible inverse latex which can advantageously comprise the surfactant composition (C) as defined above, within the ($S_2$) of oil-in-water (O/W) type, is, for example, a composition comprising, per 100% by weight:
a) from 20% by weight to 80% by weight of a crosslinked and/or branched anionic polyelectrolyte (P) obtained by polymerization:
  of at least one neutral monomer chosen in particular from acrylamide, N,N-dimethylacrylamide, N-[2-hydroxy-1,1-bis(hydroxymethyl)ethyl]propenamide [or tris(hydroxymethyl)acrylamidomethane or N-[tris(hydroxymethyl)methyl]acrylamide, also known as THAM] or 2-hydroxyethyl acrylate;
  and/or
  of at least one monomer comprising a strong acid functional group;
  and/or
  of at least one monomer comprising a weak acid functional group;
  and/or
  of at least one neutral monomer of formula (I):

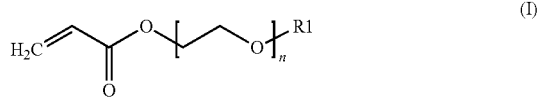

in which the R1 radical represents a linear or branched aliphatic radical comprising from 8 to 20 carbon atoms and n represents an integer of greater than or equal to one and less than or equal to thirty;
b) from 5% by weight to 10% by weight of an emulsifying system ($S_1$) of water-in-oil (W/O) type;
c) from 1% by weight to 10% by weight of an emulsifying system ($S_2$) of oil-in-water (O/W) type comprising a non-zero proportion by weight of said surfactant composition (C) as defined above;
d) from 5% by weight to 45% by weight of at least one oil, and
e) from 0% by weight to 45% by weight of water.

The term "saturated or unsaturated and linear or branched aliphatic radical comprising from 6 to 20 carbon atoms" denotes, for the R1 radical in the formula (I) as defined above, more particularly the linear radicals, such as, for example, the hexyl, octyl, nonyl, decyl, undecyl, dodecyl, tetradecyl, hexadecyl, octadecyl or eicosyl radicals.

In the composition as defined above, the emulsifying system ($S_1$) of water-in-oil (W/O) type is composed either of just one surfactant or of a mixture of surfactants, provided that said surfactant or said mixture has an HLB value which is sufficiently low to bring about water-in-oil emulsions. An emulsifying agent of water-in-oil type is, for example, sorbitan esters, such as sorbitan oleate, such as that sold by Seppic under the name Montane™ 80, sorbitan isostearate, such as that sold by Seppic under the name Montane™ 70, or sorbitan sesquiolate, such as that sold by Seppic under the name Montane™ 83. There are also some polyethoxylated sorbitan esters, for example pentaethoxylated sorbitan monooleate, such as that sold by Seppic under the name Montanox™ 81, or pentaethoxylated sorbitan isostearate, such as that sold under the name Montanox™ 71 by Seppic. There is also diethoxylated oleocetyl alcohol, such as that sold under the name Simulsol™ OC 72 by Seppic, polyesters with a molecular weight of between 1000 and 3000, products of the condensation between a polyisobutenyl succinic acid or its anhydride, such as Hypermer™ 2296, sold by Uniqema, or finally block copolymers with a molecular weight of between 2500 and 3500, such as Hypermer™ B246, sold by Uniqema, or Simaline™ IE 200, sold by Seppic.

In the context of this use, the surfactant composition (C) as defined above can be employed, alone or as a mixture with at least one other emulsifying agent of oil-in-water (O/W) type, within said emulsifying system ($S_2$) of oil-in-water (O/W) type, inverting agent for self-invertible inverse latexes.

According to a specific form of the self-invertible inverse latexes as defined above, the emulsifying system ($S_2$) of oil-in-water (O/W) type consists of 100% by weight of said surfactant composition (C) as defined above.

According to another specific form of the self-invertible inverse latexes as defined above, the emulsifying system ($S_2$) of oil-in-water (O/W) type additionally comprises at least one emulsifying surfactant of the (O/W) type other than one or other of the compounds constituting said surfactant composition (C) as defined above.

The term "emulsifying agent of the oil-in-water type" denotes emulsifying agents having an HLB value which is sufficiently high to provide oil-in-water emulsions, such as ethoxylated sorbitan esters, such as sorbitan oleate polyethoxylated with 20 mol of ethylene oxide, sold by Seppic under the name Montanox™ 80, sorbitan laurate polyethoxylated with 20 mol of ethylene oxide, sold by Seppic under the name of Montanox™ 20, castor oil polyethoxylated with 40 mol of ethylene oxide, sold under the name Simulsol™ OL 50, decaethoxylated oleodecyl alcohol, sold by Seppic under the name Simulsol™ OC 710, heptaethoxylated lauryl alcohol, sold under the name Simulsol™ P7, decaethoxylated nonylphenol, sold by Seppic under the name Nonarox™-10-30, or polyethoxylated sorbitan hexaoleates, sold by Seppic under the name Simaline™ IE 400.

According to a more particular form of the self-invertible inverse latexes as defined above, the emulsifying system ($S_2$) of oil-in-water (O/W) type additionally comprises a non-zero proportion by weight of at least one emulsifying agent of the oil-in-water type chosen from sorbitan oleate polyethoxylated with 20 mol of ethylene oxide, sorbitan laurate polyethoxylated with 20 mol of ethylene oxide, castor oil polyethoxylated with 40 mol of ethylene oxide, decaethoxylated oleodecyl alcohol, heptaethoxylated lauryl alcohol, decaethoxylated nonylphenol or polyethoxylated sorbitan hexaoleates. According to this specific form, said emulsifying system ($S_2$) comprises at least 30% by weight of said mixture (M) as defined above.

According to a very specific form of the self-invertible invert latexes as defined above, the emulsifying system ($S_2$) of oil-in-water type comprises, per 100% of its weight:

from 10% by weight to 40% by weight of heptaethoxylated lauryl alcohol and from 60% by weight to 90% by weight of the surfactant composition (C) as defined above.

The term "crosslinked polyelectrolyte" denotes, for (P), a non-linear polyelectrolyte which is provided in the form of a three-dimensional network insoluble in water but swellable with water and which thus results in a chemical gel being obtained.

The term "branched polyelectrolyte" denotes, for (P), a non-linear polymer which has pendent chains, so as to obtain, when this polymer is dissolved in water, a high state of entanglement, resulting in very high viscosities with a low gradient.

The polyelectrolyte (P) is more particularly crosslinked with a diethylenic or polyethylenic compound in the molar proportion, expressed with respect to the monomers employed, of generally less than or equal to 0.40 mol %, mainly of less than 0.25 mol %, more particularly of less than or equal to 0.05 mol % and very particularly of between 0.005 mol % and 0.01 mol %. Preferably, the crosslinking agent and/or the branching agent is chosen from ethylene glycol dimethacrylate, diethylene glycol diacrylate, sodium diallyloxyacetate, ethylene glycol diacrylate, diallylurea, triallylamine, trimethylolpropane triacrylate, methylenebisacrylamide or a mixture of these compounds.

Examples of constituent crosslinked polyelectrolytes (P) of said self-invertible inverse latexes include:

crosslinked terpolymers of acrylic acid, partially salified in the sodium salt or ammonium salt form, of acrylamide and of tetraethoxylated lauryl acrylate;

crosslinked terpolymers of 2-methyl-2-[(1-oxo-2-propenyl)amino]-1-propanesulfonic acid, partially salified in the sodium salt form, of acrylamide and of tetraethoxylated lauryl acrylate;

crosslinked terpolymers of 2-methyl-2-[(1-oxo-2-propenyl)amino]-1-propanesulfonic acid, partially salified in the sodium salt form, of acrylic acid, partially salified in the sodium salt form, and of tetraethoxylated lauryl acrylate;

crosslinked terpolymers of 2-methyl-2-[(1-oxo-2-propenyl)amino]-1-propanesulfonic acid, partially salified in the sodium salt form, of 2-hydroxyethyl acrylate and of tetraethoxylated lauryl acrylate;

crosslinked copolymers of 2-methyl-2-[(1-oxo-2-propenyl)amino]-1-propanesulfonic acid, partially salified in the sodium salt form, and of tetraethoxylated lauryl acrylate;

crosslinked copolymers of acrylic acid, partially salified in the ammonium salt or monoethanolamine salt form, and of tetraethoxylated lauryl acrylate;

crosslinked tetrapolymers of acrylamide, of 2-methyl-2-[(1-oxo-2-propenyl)amino]-1-propanesulfonic acid, partially salified in the sodium salt form, of acrylic acid, partially salified in the sodium salt form, and of tetraethoxylated lauryl acrylate;

tetrapolymers of 2-methyl-2-[(1-oxo-2-propenyl)amino]-1-propanesulfonic acid, partially salified in the sodium salt form, of acrylamide, of vinylpyrrolidone and of tetraethoxylated lauryl acrylate; and crosslinked pentapolymers of 2-methyl-2-[(1-oxo-2-propenyl)amino]-1-propanesulfonic acid, partially or completely salified in the sodium salt form, of acrylic acid, partially salified in the sodium salt form, of 2-hydroxyethyl acrylate, of tris(hydroxymethyl)aminomethylacrylamide and of tetraethoxylated lauryl acrylate.

The constituent crosslinked anionic polyelectrolyte (P) of said self-invertible inverse latexes comprises, per 100% of monomers employed, more particularly:

from 20 mol % to 80 mol % of monomer units resulting from a monomer comprising either a strong acid functional group or a weak acid functional group;

from 15 mol % to 75 mol % of monomer units resulting from a neutral monomer other than the compound of formula (I) as defined above;

from 0.5 mol % to 5 mol % of monomer units resulting from a monomer of formula (I) as defined above.

According to another specific aspect, the crosslinked anionic polyelectrolyte (P) comprises, per 100% of monomers employed:

from 55 mol % to 80 mol % of monomer units resulting from a monomer comprising a strong acid functional group;

from 15 mol % to 40 mol % of monomer units resulting from a neutral monomer other than the compound of formula (I) as defined above;

from 1 mol % to 5 mol % of monomer units resulting from a monomer of formula (I) as defined above.

According to another specific form, said self-invertible inverse latex as defined above comprises more than 60% by weight and at most 70% by weight of anionic polyelectrolyte (P).

In said self-invertible inverse latexes as defined above, the oil phase is composed either of a commercial mineral oil comprising saturated hydrocarbons, such as paraffins, isoparaffins or cycloparaffins, exhibiting, at ambient temperature, a density between 0.7 and 0.9 and a boiling point of greater than approximately 250° C., such as, for example, Marcol™ 52, sold by Exxon Chemical, or of a vegetable oil, such as squalane of vegetable origin, or a synthetic oil, such as hydrogenated polyisobutene or hydrogenated polydecene, or of a mixture of several of these oils. Marcol™ 52 is a commercial oil corresponding to the definition of liquid paraffins of the Codex français [French Pharmacopeia]. This is a white mineral oil in accordance with the FDA 21 CFR 172.878 and CFR 178.3620 (a) regulations and it is registered in the USA Pharmacopeia, US XXIII (1995), and in the European Pharmacopoeia (1993). The composition as defined above can also comprise various additives, such as complexing agents, chain-transfer agents or chain-limiting agents.

The aim of the examples which follow is to illustrate the present invention without, however, limiting it.

EXAMPLE A

Preparation of a Surfactant Composition (C) Employed in the Composition which is a Subject Matter of the Present Invention Stage A1): Preparation of the Intermediate Composition (C')
21 100 g of a mixture of fatty alcohols, comprising from 65% by weight to 75% by weight of alkanol comprising 12 carbon atoms, from 21% by weight to 28% by weight of alkanol comprising 14 carbon atoms and from 4% by weight to 8% by weight of alkanol comprising 16 carbon atoms, heated beforehand, are introduced into a reactor, are kept stirred and are dried. 326 grams of 50% boron trifluoride in diethyl ether are subsequently added and then 32 600 g of 3-(hydroxymethyl)-3-ethyloxetane are gradually added with stirring over 4 hours, the temperature being maintained at approximately 110° C. The reaction medium is then left at 115° C. for a further 11 hours. The expected composition (C') is then obtained, which composition is characterized as follows:

Appearance at 25° C.: Cloudy gel
Acid number (in mg KOH/g; NFT60-204): 3.9
Hydroxyl number (in mg KOH/g): 400.5
Content by weight of free 2-(hydroxymethyl)-2-ethyloxetane (determined by gas chromatography): <0.05%
Content by weight of free alkanols (determined by gas chromatography): $C_{12}$ alkanol: 5.7%; $C_{14}$ alkanol: 2.0%; $C_{16}$ alkanol: 0.5%.

Stage A2): Preparation of the Surfactant Composition (C)

50 000 g of the intermediate composition (C') obtained in the preceding stage A1) are introduced with 75 g of potassium hydroxide into an autoclave with a capacity of 0.1 m³ and are then dried at a temperature of 105° C. An amount of 35 000 g of ethylene oxide is subsequently gradually introduced while regulating the temperature of the reaction mixture at a value of 125° C. Once the total amount of ethylene oxide has been introduced, the reaction mixture is kept stirred at 125° C. for an additional period of time of one hour. The product then obtained is subsequently cooled to a temperature of 80° C. and emptied out. The surfactant composition (C) is then obtained, which composition is characterized as follows:

Appearance at 30° C.: clear liquid
Color: 125 Alpha
Hydroxyl number (in mg KOH/g): 252.5
Acid number (in mg KOH/g) (NFT60-204): 0.08
Residual water content: 0.05%
Cloud point (NF EN 1890E): 76° C.
Content by weight of free alkanols (gas chromatography): $C_{12}$ alkanol: 1.2%; $C_{14}$ alkanol: 0.4%; $C_{16}$ alkanol: 0.1%, i.e., in total, 1.7% of residual alkanols
Viscosity at 25° C. (Brookfield LVT, Rotor 3, Speed 12): 1 072 mPa·s Example 1 (According to the Invention)

Self-Invertible Inverse Latex of the ATBS (Na Salt)/HEA/(LA-4EO) [ATBS/HEA/(LA-4EO) 89.0/9.9/1.1 Molar] Copolymer Crosslinked with MBA 1) Preparation
  a)—The following are successively introduced with stirring into a first beaker:
    672.5 g of a 55% by weight commercial solution of sodium salt of 2-acrylamido-2-methylpropanesulfonic acid (ATBS Na),
    20.8 g of 2-hydroxyethyl acrylate (HEA);
    0.028 g of methylenebisacrylamide (MBA); and
    1.0 g of a 40% by weight commercial solution of sodium diethylenetriaminepentaacetate.
  The pH is then adjusted to 4 therein by adding, if necessary, the required amounts of 2-acrylamido-2-methylpropanesulfonic acid and deionized water up to 700 g.
  b)—The following are successively introduced with stirring into a second beaker:
    130 g of polyisobutene,
    30 g of Marcol™ 52,
    90 g of Isopar™ H,
    17 g of Montane™ 70,
    3 g of Hypermer™ 6212,
    5 g of Simaline™ IE 200,
    7.2 g of tetraethoxylated lauryl acrylate (commercial) (LA-4EO),
    0.36 g of dilauroyl peroxide
  c)—The aqueous phase is then incorporated in the organic phase with stirring and then the preemulsion thus obtained is subjected to shearing mechanical stirring using a rotor agitator of Silverson type so as to create a fine emulsion while sparging with nitrogen.
  d)—After cooling to approximately 8° C., the polymerization reaction is initiated using the oxidation/reduction couple: cumene hydroperoxide/sodium metabisulfite.
  e)—Once the polymerization reaction is complete, the Isopar™ H and virtually all of the water are removed by vacuum distillation.
  f)—After introduction of 2% by weight of Laureth-7 and 4% by weight of the surfactant composition (C) obtained in example A, the self-invertible inverse latex (1) is obtained, which latex comprises approximately 63% of polymer, which is not very viscous, which inverts very rapidly in water and which has a high thickening power. Furthermore, this inverse latex is very stable as no phenomenon of syneresis is observed, in that only a very small amount of oil is released and that polymer does not sediment out. Its water content, measured by Karl-Fischer titrimetry, is 1.8% by weight.

2) Viscosity Measurements
  a)—The viscosity of the self-invertible inverse latex (1) obtained as indicated in section 1, that of an aqueous solution devoid of sodium chloride (Sol.1) and those of aqueous solutions respectively comprising 0.1% by weight (Sol.2) and 1% by weight (Sol.3) of sodium chloride are measured, said aqueous solutions each comprising 2% by weight of said self-invertible inverse latex (1). The results measured using a Brookfield RVT viscometer are recorded in the following table:

|  | Rotor (R); Rotational speed of the rotor (S) (in revolutions per minute) | Viscosity (in mPa · s) |
|---|---|---|
| Inverse latex (1) | R 3, S 20 | 2700 |
| Sol. 1 | R 6, S 5 | 54 000 |
| Sol. 2 | R 6, S 5 | 27 000 |
| Sol. 3 | R 3, S 5 | 1600 |

3) Measurement of the Inversion Time and Evaluation of the Stability of the Inverse Latex
  a)—The inversion time is evaluated by measuring the time necessary to obtain a smooth and homogeneous gel for a 2% by weight aqueous solution of self-invertible inverse latex (1) under the standard conditions for measuring this viscosity, that is to say by incorporating 16 g of the inverse latex (1) in 784 g of water, the combined mixture being placed in a 1 liter low-form beaker, and by then stirring the combined mixture using a butterfly-type axial-flow impeller rotating at 150 revolutions per minute. The inversion time is thus a period of time evaluated between starting the stirrer and the appearance of a smooth and homogeneous medium in the beaker. In the present example, the inversion time is 50 seconds.
  b)—The stability of the inverse latex is evaluated by observing the time for appearance of an oil layer at the surface. In the present example, the time for appearance of the oil layer at the surface of the inverse latex (1) is two weeks.

Example T1 (According to the State of the Art)

Self-Invertible Inverse Latex of the ATBS(Na Salt)/HEA/(LA-4EO) [ATBS/HEA/(LA-4EO) 89.0/9.9/1.1 Molar] Copolymer Crosslinked with MBA 1) Preparation Stages a) to d) of example 1 are reproduced. In stage f), 4% by weight of Montanox™ 20 are added in place of 4% by weight of the surfactant composition (C) and the self-invertible inverse latex (T1) is obtained.

2) Viscosity Measurements
  a)—The viscosity of the self-invertible inverse latex (T1) obtained as indicated in section 1, that of an aqueous solution devoid of sodium chloride (Sol.4) and those of aqueous solutions respectively comprising 0.1% by weight (Sol.5) and 1% by weight (Sol.6) of sodium chloride are measured, said aqueous solutions each comprising 2% by weight of said self-invertible inverse latex (T1). The results measured using a Brookfield RVT viscometer are recorded in the following table:

|  | Rotor (R); Rotational speed of the rotor (S) (in revolutions per minute) | Viscosity (in mPa · s) |
| --- | --- | --- |
| Inverse latex (T1) | R 3, S 20 | 2900 |
| Sol. 4 | R 6, S 5 | 51 200 |
| Sol. 5 | R 6, S 5 | 25 200 |
| Sol. 6 | R 3, S 5 | 1300 |

3) Measurement of the Inversion Time and Evaluation of the Stability of the Inverse Latex
  a)—The inversion time, evaluated in the same way as in the preceding example, is 2 minutes 20 seconds.
  b)—The stability of the inverse latex (T1) is evaluated in the same way as in the preceding example. Significant release of oil is observed after one week.

Example 2 (According to the Invention)

Self-Invertible Inverse Latex of the ATBS(Na Salt)/HEA/(LA-4EO) [ATBS/HEA/(LA-4EO) 89.0/9.9/1.1 Molar] Copolymer Crosslinked with MBA 1) Preparation Stages a) to d) of example 1 are reproduced. In stage f), only 4% by weight of the surfactant composition (C) are added and the self-invertible inverse latex (2) is obtained.

2) Viscometry, Measurement of the Inversion Time and Evaluation of the Stability of the Inverse Latex (2)
  a)—The viscometric performance of the inverse latex (2) is similar to that reported for the inverse latex of example 1.
  b)—The inversion time of the inverse latex (2), evaluated in the same way as in example 1, is approximately 40 seconds.
  c)—The stability of the inverse latex (2) is evaluated in the same way as in example 1. The time for the appearance of the oil layer is a few days.

Example T2 (According to the State of the Art)

Self-Invertible Inverse Latex of the ATBS(Na Salt)/HEA/(LA-4EO) [ATBS/HEA/(LA-4EO) 89.0/9.9/1.1 Molar] Copolymer Crosslinked with MBA 1) Preparation Stages a) to d) of example 1 are reproduced. In stage f), 4% by weight of a composition (C''') are added, which composition comprises, per 100 mol %:
  i) a proportion of greater than or equal to 10 mol % and less than or equal to 50 mol % of a compound of formula (II''') corresponding to the formula (II) in which R2 represents a linear or branched alkyl radical comprising 10 carbon atoms and in which the sum m1+m2+m3 is equal to 5;
  ii) a proportion of greater than or equal to 50 mol % and less than or equal to 90 mol % of a compound of formula (III''') or of its isomer of formula (IV''') or of the mixture of these two isomers, formulae (III''') and (IV''') respectively corresponding to the formulae (III) and (IV) in which R2 represents a linear or branched alkyl radical comprising 10 carbon atoms and in which the sum m4+m5+m6+m7 is equal to 5;
and the self-invertible inverse latex (T2) is obtained.

2) Viscometry, Measurement of the Inversion Time and Evaluation of the Stability of the Inverse Latex (T2)
  a)—The viscometric performance of the inverse latex (T2) is similar to that reported for the inverse latex of example 1.
  b)—The inversion time of the inverse latex (T2), evaluated in the same way as in example 1, is approximately 50 seconds.
  c)—The stability of the inverse latex (T2) is evaluated in the same way as in example 1. The time for appearance of the oil layer is a few hours.

Example T3 (According to the State of the Art)

Self-Invertible Inverse Latex of the AM/AA/(LA-4EO) [AM/AA/(LA-4EO) 24.7/74.1/1.2 Molar] Copolymer Crosslinked with MBA 1) Preparation
  a)—The following are successively introduced with stirring into a first beaker:
    106.5 g of a 50% (by weight) commercial solution of acrylamide (AM),
    162.0 g of glacial acrylic acid (AA),
    98.1 g of a 29.3% by weight aqueous ammonia solution,
    0.047 g of methylenebisacrylamide (MBA),
    0.45 g of a 40% commercial solution of sodium diethylenetriaminepentaacetate,
    deionized water up to 680 g.
  b)—The following are successively introduced with stirring into a second beaker:
    121 g of polyisobutene,
    28 g of Marcol™ 52,
    99 g of Isopar™ H,
    17 g of Montane™ 70,
    3 g of Hypermer™ 2296,
    5 g of Simaline™ IE 200,
    1.2 g of tetraethoxylated lauryl acrylate (commercial) (LA-4EO),
    0.1 g of AIBN.

c)—The aqueous phase is then incorporated in the organic phase with stirring and then the preemulsion thus obtained is subjected to shearing mechanical stirring using a rotor agitator of Silverson type so as to create a fine emulsion while sparging with nitrogen.

d)—After cooling to approximately 8° C., the polymerization reaction is initiated using the oxidation/reduction couple: cumene hydroperoxide/sodium metabisulfite.

e)—Once the polymerization reaction is complete, the Isopar™ H and virtually all of the water are removed by vacuum distillation.

f). After introduction of 4% of Montanox™ 20 and 2% of Laureth-7, the self-invertible inverse latex (T3) is obtained, which latex comprises approximately 63% of polymer, which is not very viscous, which inverts very rapidly in water and which has a high thickening power. Its water content, measured by Karl-Fischer titrimetry, is 1.8% by weight.

2) Viscosity Measurements a)—The viscosity of the self-invertible inverse latex (T3) obtained as indicated in section 1, that of an aqueous solution devoid of sodium chloride (Sol.7) and those of aqueous solutions respectively comprising 0.1% by weight (Sol.8) and 1% by weight (Sol.9) of sodium chloride are measured, said aqueous solutions each comprising 2% by weight of said self-invertible inverse latex (T3). The results measured using a Brookfield RVT viscometer are recorded in the following table:

|  | Rotor (R); Rotational speed of the rotor (S) (in revolutions per minute) | Viscosity (in mPa·s) |
| --- | --- | --- |
| Inverse latex (T3) |  | nd |
| Sol. 7 | R 6, S 5 | 79 400 |
| Sol. 8 | R 6, S 5 | 45 200 |
| Sol. 9 | R 3, S 5 | 3300 | nd: not determined

3) Measurement of the Inversion Time and Evaluation of the Stability of the Inverse Latex (T3)

b)—The inversion time of the inverse latex (T3), evaluated in the same way as in example 1, is approximately 2 minutes.

c)—The stability of the inverse latex (T3) is evaluated in the same way as in example 1. The time for appearance of the oil layer is two weeks.

Example 3 (According to the Invention)

Self-Invertible Inverse Latex of the AM/AA/(LA-4EO) [AM/AA/(LA-4EO) 24.7/74.1/1.2 Molar] Copolymer Crosslinked with MBA 1) Preparation Stages a) to d) of example T3 are reproduced. In stage f), 2% by weight of Laureth-7 and 4% by weight of the surfactant composition (C) are added in place of the 4% of Montanox™ 20 and 2% of Laureth-7 of said example T3 and the self-invertible inverse latex (3) is obtained.

2) Viscometry, Measurement of the Inversion Time and Evaluation of the Stability of the Inverse Latex (3)

a)—The viscometric performance of the inverse latex (3) is similar to that reported for the inverse latex of example T3.

b)—The inversion time of the inverse latex (3), evaluated in the same way as in example 1, is approximately 30 seconds.

c)—The stability of the inverse latex (3) is evaluated in the same way as in example 1. The time for appearance of the first oil drops is three weeks.

Example 4 (According to the Invention)

Self-Invertible Inverse Latex of the ATBS (Na Salt)/AA/HEA/THAM/(LA-4EO) [ATBS/AA/HEA/THAM/(LA-4EO) 83.9/1.9/9.3/3.7/1.2 Molar] Copolymer Crosslinked with MBA 1) Preparation a)—The following are successively introduced with stirring into a first beaker:

672.5 g of a 55% (by weight) commercial solution of the sodium salt of 2-acrylamido-2-methylpropanesulfonic acid (ATBS Na);

20.8 g of 2-hydroxyethyl acrylate;

12.6 g of THAM;

2.6 g of acrylic acid (AA);

0.041 g of methylenebisacrylamide (MBA);

0.45 g of a 40% commercial solution of sodium diethylenetriaminepentaacetate.

The pH is then adjusted therein to 4 by adding, if necessary, the required amount of 2-acrylamido-2-methylpropanesulfonic acid and deionized water up to 700 g.

b)—The following are successively introduced with stirring into a second beaker:

130 g of polyisobutene, 30 g of Marcol™ 52, 90 g of Isopar™ H, 17 g of Montane™ 70, 5 g of Hypermer™ 6212, 3 g of Dehymuls PGPH (polyglyceryl polyhydroxystearate), 7.4 g of tetraethoxylated lauryl acrylate (commercial) (LA-4EO), 0.14 g of dilauroyl peroxide.

c)—The aqueous phase is then incorporated in the organic phase with stirring and then the preemulsion thus obtained is subjected to shearing mechanical stirring using a rotor agitator of Silverson type so as to create a fine emulsion while sparging with nitrogen.

d)—After cooling to approximately 8° C., the polymerization reaction is initiated using the oxidation/reduction couple: cumene hydroperoxide/sodium metabisulfite.

e)—Once the polymerization reaction is complete, the Isopar™ H and virtually all of the water are removed by vacuum distillation.

f)—After introduction of 2% by weight of Laureth-7 and 4% by weight of the surfactant composition (C) obtained in example A, the self-invertible inverse latex (4) is obtained, which latex comprises approximately 63% of polymer, which is not very viscous, which inverts very rapidly in water and which has a high thickening power. Its water content, measured by Karl-Fischer titrimetry, is 2.2% by weight.

2) Viscosity Measurements a)—The viscosity of the self-invertible inverse latex (4) obtained as indicated in section 1, that of an aqueous solution devoid of sodium chloride (Sol.10) and that of an aqueous solution comprising 0.1% by weight (Sol.11) of sodium chloride are measured, said aqueous solutions each comprising 2% by weight of said self-invertible inverse latex (4). The results, measured using a Brookfield RVT viscometer, are recorded in the following table:

| | Rotor (R); Rotational speed of the rotor (S) (in revolutions per minute) | Viscosity (in mPa·s) |
|---|---|---|
| Inverse latex (4) | R 3, S 20 | 1100 |
| Sol. 10 | R 6, S 5 | 66 200 |
| Sol. 11 | R 6, S 5 | 16 500 | nd: not determined

3) Measurement of the Inversion Time and Evaluation of the Stability of the Inverse Latex
- b)—The inversion time of the inverse latex (4), evaluated in the same way as in example 1, is approximately 30 seconds.
- c)—The stability of the inverse latex (4) is evaluated in the same way as in example 1. The time for appearance of the first oil drops is three weeks.

The invention claimed is:

1. A self invertible inverse latex comprising as an inverting agent a surfactant composition (C), alone or as a mixture with other emulsifying agents capable of preparing an oil-in-water (O/W) emulsifying system), said surfactant composition (C) comprising, per 100 mol %:
1) a proportion of greater than or equal to 10 mol % and of less than or equal to 50 mol % of a composition ($C_{II}$) comprising, per 100 mol %:
α) from 60 mol % to 100 mol % of a compound of formula (II):

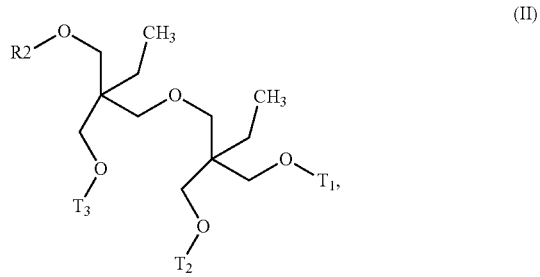

(II)

in which:
R2 represents a linear or branched alkyl radical comprising 12 carbon atoms,
$T_1$ represents a hydrogen atom or a (—$CH_2$—$CH_2$—O—)$_{m1}$—H radical in which m1 is an integer of greater than or equal to zero and less than or equal to ten,
$T_2$, which is identical to or different from $T_1$, represents a hydrogen atom or a (—$CH_2$—$CH_2$—O—)$_{m2}$—H radical in which m2 is an integer of greater than or equal to zero and less than or equal to ten, and
$T_3$, which is identical to or different from $T_1$ and $T_2$, represents a hydrogen atom or a (—$CH_2$—$CH_2$—O—)$_{m3}$—H radical in which m3 is an integer of greater than or equal to zero and less than or equal to ten,
wherein m1 +m2 +m3 is greater than 0 and less than or equal to ten;

β) optionally up to 40 mol % of a compound of formula (II'):

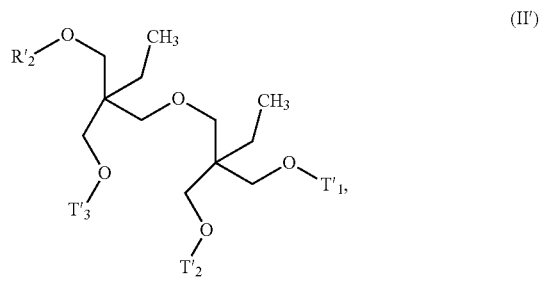

(II')

in which:
$R'_2$ represents a linear or branched alkyl radical comprising 14 carbon atoms,
$T'_1$ represents a hydrogen atom or a (—$CH_2$—$CH_2$—O—)$_{m1}$—H radical in which m1 is an integer of greater than or equal to zero and less than or equal to ten,
$T'_2$, which is identical to or different from $T'_1$, represents a hydrogen atom or a (—$CH_2$—$CH_2$—O—)$_{m2}$—H radical in which m2 is an integer of greater than or equal to zero and less than or equal to ten, and
$T'_3$, which is identical to or different from $T'_1$ and $T'_2$, represents a hydrogen atom or a (—$CH_2$—$CH_2$—O—)$_{m3}$—H radical in which m3 is an integer of greater than or equal to zero and less than or equal to ten,
wherein the sum m1 +m2 +m3 is greater than 0 and less than or equal to ten; and γ) optionally up to 10 mol % of a compound of formula (II"):

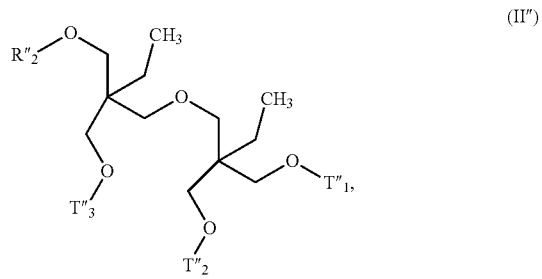

(II")

in which:
$R''_2$ represents a linear or branched alkyl radical comprising 16 carbon atoms,
$T''_1$ represents a hydrogen atom or a (—$CH_2$—$CH_2$—O—)$_{m1}$—H radical in which m1 is an integer of greater than or equal to zero and less than or equal to ten,
$T''_2$, which is identical to or different from $T''_1$, represents a hydrogen atom or a (—$CH_2$—$CH_2$—O—)$_{m2}$—H radical in which m2 is an integer of greater than or equal to zero and less than or equal to ten, and
$T''_3$, which is identical to or different from $T''_1$ and $T''_2$, represents a hydrogen atom or a (—$CH_2$—$CH_2$—

O—)$_{m3}$—H radical in which m3 is an integer of greater than or equal to zero and less than or equal to ten, Wherein the sum m1 +m2 +m3 is greater than 0 and less than or equal to ten;

2) a proportion of greater than or equal to 50 mol % and of less than or equal to 90 mol % of a composition (C$_{III}$) comprising, per 100 mol %:

α) from 60 mol % to 100 mol % of a compound of formula (III):

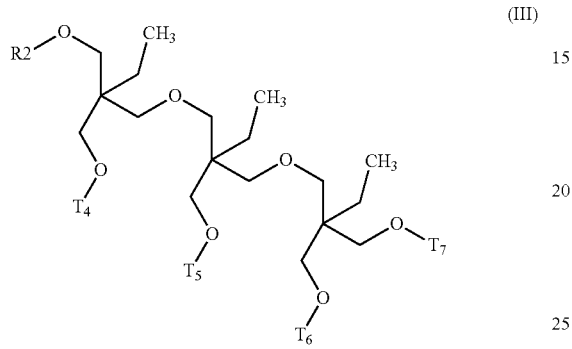

(III)

or of its isomer of formula (IV):

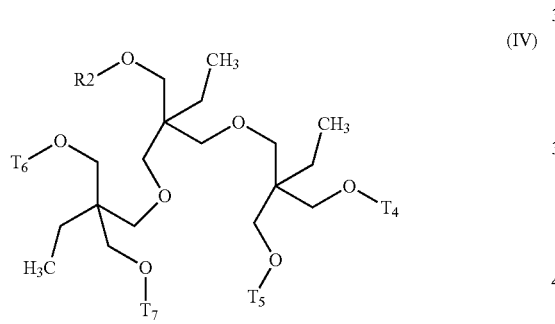

(IV)

or of the mixture of these two isomers, in which formulae (III) and (IV):

R2 represents a linear or branched alkyl radical comprising 12 carbon atoms, T$_4$ represents a hydrogen atom or a (—CH$_2$—CH$_2$—O—)$_{m4}$—H radical in which m4 is an integer of greater than or equal to zero and less than or equal to ten, T$_5$, which is identical to or different from T$_4$, represents a hydrogen atom or a (—CH$_2$—CH$_2$—O—)$_{m5}$—H radical in which m5 is an integer of greater than or equal to zero and less than or equal to ten, T$_6$, which is identical to or different from T$_4$ and T$_5$, represents a hydrogen atom or a (—CH$_2$—CH$_2$—O—)$_{m6}$—H radical in which m6 is an integer of greater than or equal to zero and less than or equal to ten, T$_7$, which is identical to or different from T$_4$, T$_5$ and T$_6$, represents a hydrogen atom or a (—CH$_2$—CH$_2$—O—)$_{m7}$—H radical in which m7 is an integer of greater than or equal to zero and less than or equal to ten, wherein the sum m4 +m5 +m6 +m7 is greater than 0 and less than or equal to ten;

β) optionally up to 40 mol % of a compound of formula (III'):

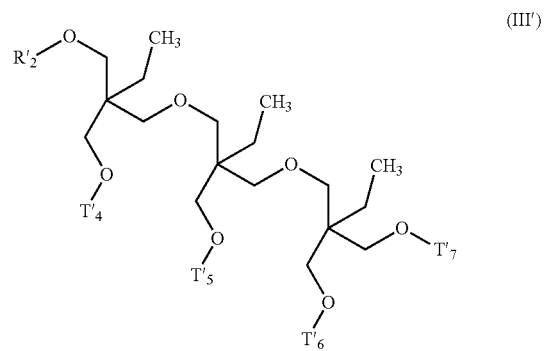

(III')

or of its isomer of formula (IV'):

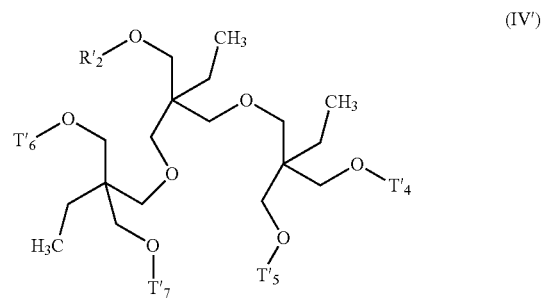

(IV')

or of the mixture of these two isomers, in which formulae (III') and (IV'):

R'$_2$ represents a linear or branched alkyl radical comprising 14 carbon atoms, T'$_4$ represents a hydrogen atom or a (—CH$_2$—CH$_2$—O—)$_{m4}$—H radical in which m4 is an integer of greater than or equal to zero and less than or equal to ten, T'$_5$, which is identical to or different from T'$_4$, represents a hydrogen atom or a (—CH$_2$—CH$_2$—O—)$_{m5}$—H radical in which m5 is an integer of greater than or equal to zero and less than or equal to ten, T'$_6$, which is identical to or different from T'$_4$ and T'$_5$, represents a hydrogen atom or a (—CH$_2$—CH$_2$—O—)$_{m6}$—H radical in which m6 is an integer of greater than or equal to zero and less than or equal to ten, and T'$_7$, which is identical to or different from T'$_4$, T'$_5$ and T'$_6$, represents a hydrogen atom or a (—CH$_2$—CH$_2$—O—)$_{m7}$—H radical in which m7 is an integer of greater than or equal to zero and less than or equal to ten, wherein the sum m4 +m5 +m6 +m7 is greater than 0 and less than or equal to ten; and γ) optionally up to 10 mol % of a compound of formula (III"):

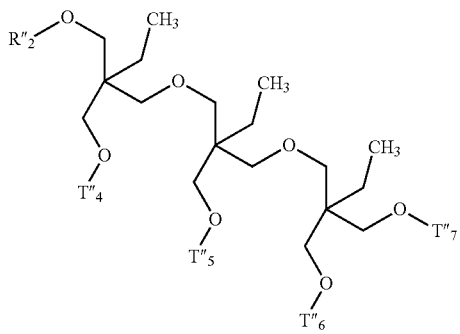

(III")

or of its isomer of formula (IV"):

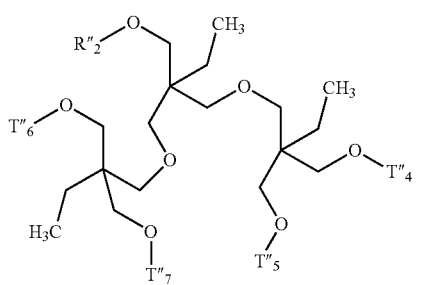

(IV")

or of the mixture of these two isomers,
in which formulae (III") and (IV"):
- R"$_2$ represents a linear or branched alkyl radical comprising 16 carbon atoms,
- T"4 represents a hydrogen atom or a (—CH$_2$—CH$_2$—O—)$_{m4}$—H radical in which m4 is an integer of greater than or equal to zero and less than or equal to ten,
- T"$_5$, which is identical to or different from T"$_4$, represents a hydrogen atom or a (—CH$_2$—CH$_2$—O—)$_{m5}$—H radical in which m5 is an integer of greater than or equal to zero and less than or equal to ten,
- T"$_6$, which is identical to or different from T"$_4$ and T"$_5$, represents a hydrogen atom or a (—CH$_2$—CH$_2$—O—)$_{m6}$—H radical in which m6 is an integer of greater than or equal to zero and less than or equal to ten, and
- T"$_7$, which is identical to or different from T"$_4$, T"$_5$ and T"$_6$, represents a hydrogen atom or a (—CH$_2$—CH$_2$—O—)$_{m7}$—H radical in which m7 is an integer of greater than or equal to zero and less than or equal to ten,
- wherein the sum m4 +m5 +m6 +m7 is greater than 0 and less than or equal to ten.

2. The self invertible inverse latex according to claim 1, wherein the surfactant composition (C) additionally comprises:

3) up to 5 mol % of a composition (C$_v$) comprising, per 100 mol %:
α) from 60 mol % to 100 mol % of a compound of formula (V):

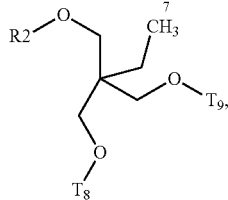

(V)

in which:
- R2 represents a linear or branched alkyl radical comprising 12 carbon atoms,
- T$_8$ represents a hydrogen atom or a (—CH$_2$—CH$_2$—O—)$_{m8}$—H radical in which m8 is an integer of greater than or equal to zero and less than or equal to ten,
- T$_9$, which is identical to or different from T$_8$, represents a hydrogen atom or a (—CH$_2$—CH$_2$—O—)$_{m9}$—H radical in which m9 is an integer of greater than or equal to zero and less than or equal to ten, and
- wherein the sum m8 +m9 is greater than 0 and less than or equal to ten;

β) -optionally up to 40 mol % of a compound of formula (V'):

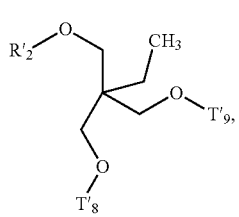

(V')

in which:
- R'$_2$ represents a linear or branched alkyl radical comprising 14 carbon atoms,
- T'$_8$ represents a hydrogen atom or a (—CH$_2$—CH$_2$—O—)$_{m8}$—H radical in which m8 is an integer of greater than or equal to zero and less than or equal to ten,
- T'$_9$, which is identical to or different from T'$_8$, represents a hydrogen atom or a (—CH$_2$—CH$_2$—O—)$_{m9}$—H radical in which m9 is an integer of greater than or equal to zero and less than or equal to ten, and
- Wherein the sum m8 +m9 is greater than 0 and less than or equal to ten; and γ) optionally up to 10 mol % of a compound of formula (V"):

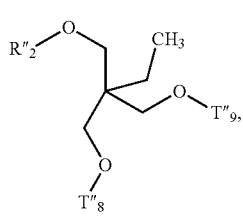

(V")

in which:
- R"$_2$ represents a linear or branched alkyl radical comprising 16 carbon atoms, T"$_8$ represents a hydrogen atom or a (—CH$_2$—CH$_2$—O—)$_{m8}$—H radical in which m8 is an integer of greater than or equal to zero and less than or equal to ten, T"$_9$, which is identical to or different from T"$_8$, represents a hydrogen atom or a (—CH$_2$—CH$_2$—O—)$_{m9}$—H radical in which m9 is an integer of greater than or equal to zero and less than or equal to ten, and wherein the sum m8 +m9 is greater than 0 and less than or equal to ten.

3. The self invertible inverse latex according to claim 1, wherein the surfactant composition (C) additionally comprises:

4) up to 5 mol % of a composition (C$_{VI}$) comprising, per 100 mol %:

α) from 60 mol % to 100 mol % of a compound of formula (VI):

in which R2 represents a linear or branched alkyl radical comprising 12 carbon atoms and m10 is an integer of greater than or equal to zero and less than or equal to ten;

α) optionally up to 40 mol % of a compound of formula (VI'):

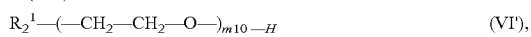

in which R'$_2$ represents a linear or branched alkyl radical comprising 14 carbon atoms and m10 is an integer of greater than or equal to zero and less than or equal to ten; and γ) optionally up to 10 mol % of a compound of formula (VI"):

in which R"$_2$ represents a linear or branched alkyl radical comprising 16 carbon atoms and m10 is an integer of greater than or equal to zero and less than or equal to ten.

4. The self invertible inverse latex according to claim 1, wherein the surfactant composition (C) comprises:

1) a proportion of greater than or equal to 20 mol % and of less than or equal to 50 mol % of the composition (C$_{II}$); and 2) a proportion of greater than or equal to 50 mol % and of less than or equal to 80 mol % of the composition (C$_{III}$).

5. The self invertible inverse latex according to claim 4, wherein:

1) said composition (C$_{II}$) comprises, per 100 mol %:

α) from 60 mol % to 80 mol % of the compound of formula (II),

β) from 15 mol % to 30 mol % of the compound of formula (II'), and

γ) up to 10 mol % of the compound of formula (II"), and 2) said composition (C$_{III}$) comprises, per 100 mol %:

α) from 60 mol % to 80 mol % of the compound of formula (III), of its isomer of formula (IV) or of the mixture of these isomers, β) from 15 mol % to 30 mol % of the compound of formula (III'), of its isomer of formula (IV') or of the mixture of these isomers, and γ) up to 10 mol % of the compound of formula (III"), of its isomer of formula (IV") or of the mixture of these isomers.

6. A surfactant composition (C), said surfactant composition (C) being an oil-in-water (O/W) emulsifying agent and comprising, per 100 mol %:

1) a proportion of greater than or equal to 10 mol % and of less than or equal to 50 mol % of a composition (C$_{II}$) comprising, per 100 mol %:

α) from 60 mol % to 100 mol % of a compound of formula (II):

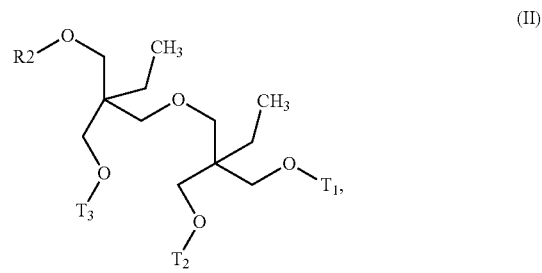

in which:

R2 represents a linear or branched alkyl radical comprising 12 carbon atoms,

T$_1$ represents a hydrogen atom or a (—CH$_2$—CH$_2$—O—)$_{m1}$—H radical in which m1 is an integer of greater than or equal to zero and less than or equal to ten, T$_2$ which is identical to or different from T$_1$, represents a hydrogen atom or a (—CH$_2$—CH$_2$—O—)$_{m2}$—H radical in which m2 is an integer of greater than or equal to zero and less than or equal to ten, and T$_3$, which is identical to or different from T$_1$ and T$_2$, represents a hydrogen atom or a (—CH$_2$—CH$_2$—O—)$_{m3}$—H radical in which m3 is an integer of greater than or equal to zero and less than or equal to ten, wherein m1 +m2 +m3 is greater than 0 and less than or equal to ten;

β) optionally up to 40 mol % of a compound of formula (II'):

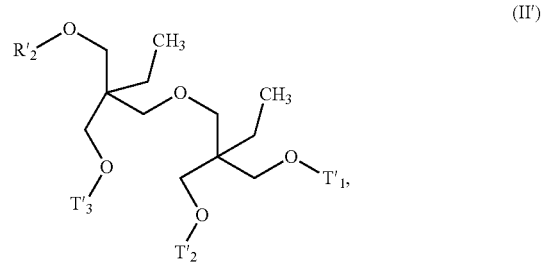

in which:

R'$_2$ represents a linear or branched alkyl radical comprising 14 carbon atoms, T'$_1$ represents a hydrogen atom or a (—CH$_2$—CH$_2$—O—)$_{m1}$—H radical in which m1 is an integer of greater than or equal to zero and less than or equal to ten, T'$_2$, which is identical to or different from T'$_1$, represents a hydrogen atom or a (—CH$_2$—CH$_2$—O—)$_{m2}$—H radical in which m2 is an integer of greater than or equal to zero and less than or equal to ten, and $T'_3$, which is identical to or different from $T'_1$ and $T'_2$, represents a hydrogen atom or a $(-CH_2-CH_2-O-)_{m3}-H$ radical in which m3 is an integer of greater than or equal to zero and less than or equal to ten, wherein the sum m1 +m2 +m3 is greater than 0 and less than or equal to ten; and γ) optionally up to 10 mol % of a compound of formula (II″):

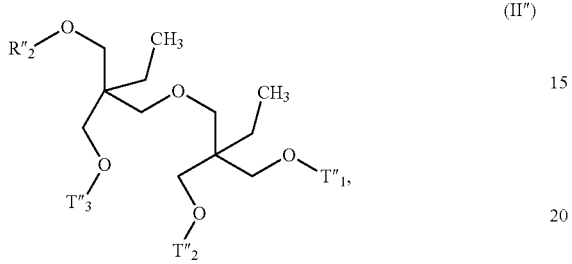

(II″)

in which:

R″$_2$ represents a linear or branched alkyl radical comprising 16 carbon atoms, T″$_1$ represents a hydrogen atom or a $(-CH_2-CH_2-O-)_{m1}-H$ radical in which m1 is an integer of greater than or equal to zero and less than or equal to ten, T″$_2$, which is identical to or different from T″$_1$, represents a hydrogen atom or a $(-CH_2-CH_2-O-)_{m2}-H$ radical in which m2 is an integer of greater than or equal to zero and less than or equal to ten, and T″$_3$, which is identical to or different from T″$_1$ and T″$_2$, represents a hydrogen atom or a $(-CH_2-CH_2-O-)_{m3}-H$ radical in which m3 is an integer of greater than or equal to zero and less than or equal to ten, Wherein the sum m1 +m2 +m3 is greater than 0 and less than or equal to ten;

2) a proportion of greater than or equal to 50 mol % and of less than or equal to 90 mol % of a composition ($C_{III}$) comprising, per 100 mol %:

α) from 60 mol % to 100 mol % of a compound of formula (III):

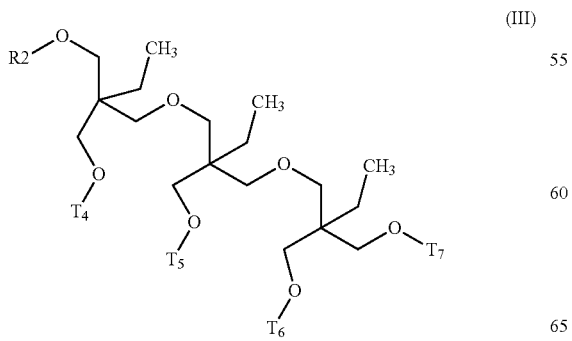

(III)

or of its isomer of formula (IV):

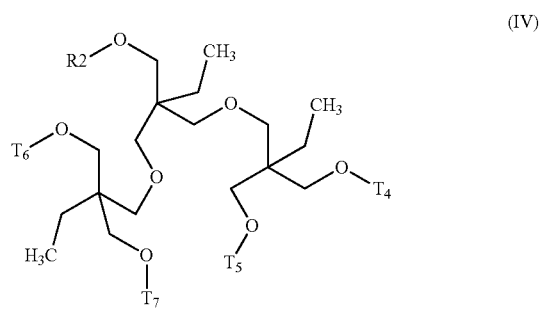

(IV)

or of the mixture of these two isomers, in which formulae (III) and (IV):

R2 represents a linear or branched alkyl radical comprising 12 carbon atoms, $T_4$ represents a hydrogen atom or a $(-CH_2-CH_2-O-)_{m4}-H$ radical in which m4 is an integer of greater than or equal to zero and less than or equal to ten, $T_5$, which is identical to or different from $T_4$, represents a hydrogen atom or a $(-CH_2-CH_2-O-)_{m5}-H$ radical in which m5 is an integer of greater than or equal to zero and less than or equal to ten, $T_6$, which is identical to or different from $T_4$ and $T_5$, represents a hydrogen atom or a $(-CH_2-CH_2-O-)_{m6}-H$ radical in which m6 is an integer of greater than or equal to zero and less than or equal to ten, $T_7$, which is identical to or different from $T_4$, $T_5$ and $T_6$, represents a hydrogen atom or a $(-CH_2-CH_2-O-)_{m7}-H$ radical in which m7 is an integer of greater than or equal to zero and less than or equal to ten, wherein the sum m4 +m5 +m6 +m7 is greater than 0 and less than or equal to ten;

β) optionally up to 40 mol % of a compound of formula (III′):

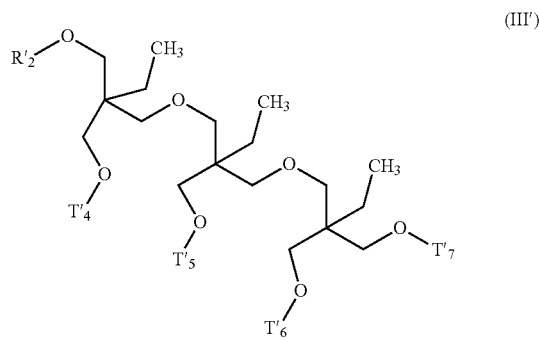

(III′)

or of its isomer of formula (IV'):

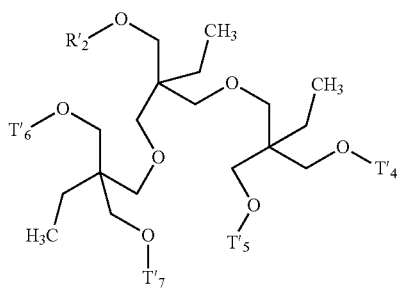

(IV')

or of the mixture of these two isomers,
in which formulae (III') and (IV'):
- $R'_2$ represents a linear or branched alkyl radical comprising 14 carbon atoms,
- $T'_4$ represents a hydrogen atom or a ($-CH_2-CH_2-O-$)$_{m4}-H$ radical in which m4 is an integer of greater than or equal to zero and less than or equal to ten,
- $T'_5$, which is identical to or different from $T'_4$, represents a hydrogen atom or a ($-CH_2-CH_2-O-$)$_{m5}-H$ radical in which m5 is an integer of greater than or equal to zero and less than or equal to ten,
- $T'_6$, which is identical to or different from $T'_4$ and $T'_5$, represents a hydrogen atom or a ($-CH_2-CH_2-O-$)$_{m6}-H$ radical in which m6 is an integer of greater than or equal to zero and less than or equal to ten, and
- $T'_7$, which is identical to or different from $T'_4$, $T'_5$ and $T'_6$, represents a hydrogen atom or a ($-CH_2-CH_2-O-$)$_{m7}-H$ radical in which m7 is an integer of greater than or equal to zero and less than or equal to ten,
- wherein the sum m4 +m5 +m6 +m7 is greater than 0 and less than or equal to ten; and γ) optionally up to 10 mol % of a compound of formula (III"):

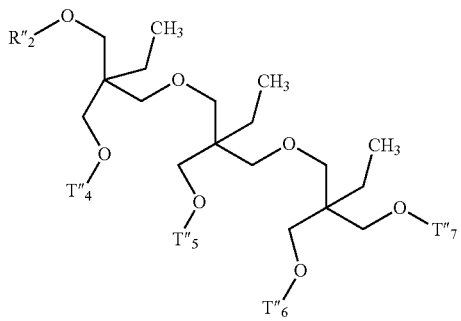

(III")

or of its isomer of formula (IV"):

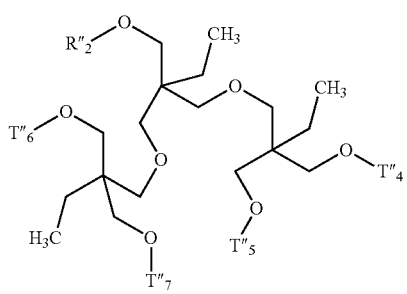

(IV")

or of the mixture of these two isomers,
in which formulae (III") and (IV"):
- $R''_2$ represents a linear or branched alkyl radical comprising 16 carbon atoms,
- $T''_4$ represents a hydrogen atom or a ($-CH_2-CH_2-O-$)$_{m4}-H$ radical in which m4 is an integer of greater than or equal to zero and less than or equal to ten,
- $T''_5$, which is identical to or different from $T''_4$, represents a hydrogen atom or a ($-CH_2-CH_2-O-$)$_{m5}-H$ radical in which m5 is an integer of greater than or equal to zero and less than or equal to ten,
- $T''_6$, which is identical to or different from $T''_4$ and $T''_5$, represents a hydrogen atom or a ($-CH_2-CH_2-O-$)$_{m6}-H$ radical in which m6 is an integer of greater than or equal to zero and less than or equal to ten, and
- $T''_7$, which is identical to or different from $T''_4$, $T''_5$ and $T'_6$, represents a hydrogen atom or a ($-CH_2-CH_2-O-$)$_{m7}-H$ radical in which m7 is an integer of greater than or equal to zero and less than or equal to ten,
- wherein the sum m4 +m5 +m6 +m7 is greater than 0 and less than or equal to ten.

7. The surfactant composition (C) according to claim 6, further comprising:
3) up to 5 mol % of a composition ($C_v$) comprising, per 100 mol %:
α) from 60 mol % to 100 mol % of a compound of formula (V):

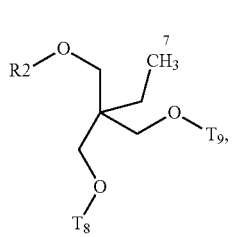

(V)

in which:
- R2 represents a linear or branched alkyl radical comprising 12 carbon atoms,
- $T_8$ represents a hydrogen atom or a ($-CH_2-CH_2-O-$)$_{m8}-H$ radical in which m8 is an integer of greater than or equal to zero and less than or equal to ten,
- $T_9$, which is identical to or different from $T_8$, represents a hydrogen atom or a ($-CH_2-CH_2-O-$)$_{m9}-H$ radical in which m9 is an integer of greater than or equal to zero and less than or equal to ten, and
- wherein the sum m8 +m9 is greater than 0 and less than or equal to ten;

β) -optionally up to 40 mol % of a compound of formula (V'):

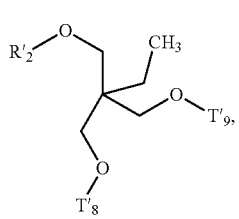

(V')

in which:

R'$_2$ represents a linear or branched alkyl radical comprising 14 carbon atoms, T'$_8$ represents a hydrogen atom or a (—CH$_2$—CH$_2$—O—)$_{m8}$—H radical in which m8 is an integer of greater than or equal to zero and less than or equal to ten, T'$_9$, which is identical to or different from T'$_8$, represents a hydrogen atom or a (—CH$_2$—CH$_2$—O—)$_{m9}$—H radical in which m9 is an integer of greater than or equal to zero and less than or equal to ten, and Wherein the sum m8 +m9 is greater than 0 and less than or equal to ten; and γ) optionally up to 10 mol % of a compound of formula (V"):

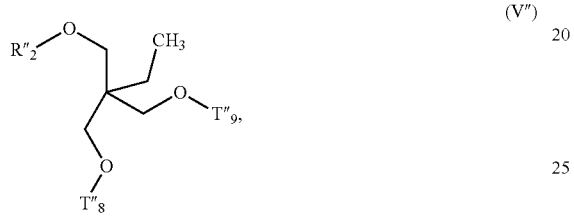

in which:

R"$_2$ represents a linear or branched alkyl radical comprising 16 carbon atoms, T"$_8$ represents a hydrogen atom or a (—CH$_2$—CH$_2$—O—)$_{m8}$—H radical in which m8 is an integer of greater than or equal to zero and less than or equal to ten, T"$_9$, which is identical to or different from T"$_8$, represents a hydrogen atom or a (—CH$_2$—CH$_2$—O—)$_{m9}$—H radical in which m9 is an integer of greater than or equal to zero and less than or equal to ten, and wherein the sum m8 +m9 is greater than 0 and less than or equal to ten.

8. The surfactant composition (C) according to claim 6, further comprising:

4) up to 5 mol % of a composition (C$_{VI}$) comprising, per 100 mol %:

α) from 60 mol % to 100 mol % of a compound of formula (VI):

$$R2\text{-}(\!-\!CH_2\!-\!CH_2\!-\!O\!-\!)_{m10}\!-\!H \qquad (VI),$$

in which R2 represents a linear or branched alkyl radical comprising 12 carbon atoms and m10 is an integer of greater than or equal to zero and less than or equal to ten;

β) optionally up to 40 mol % of a compound of formula (VI'):

$$R'_2\text{-}(\!-\!CH_2\!-\!CH_2\!-\!O\!-\!)_{m10}\!-\!H \qquad (VI'),$$

in which R'$_2$ represents a linear or branched alkyl radical comprising 14 carbon atoms and m10 is an integer of greater than or equal to zero and less than or equal to ten; and γ) optionally up to 10 mol % of a compound of formula (VI"):

$$R''_2\text{-}(\!-\!CH_2\!-\!CH_2\!-\!O\!-\!)_{m10}\!-\!H \qquad (VI''),$$

in which R"$_2$ represents a linear or branched alkyl radical comprising 16 carbon atoms and m10 is an integer of greater than or equal to zero and less than or equal to ten.

9. The surfactant composition (C) according to claim 6, comprising:

1) a proportion of greater than or equal to 20 mol % and of less than or equal to 50 mol % of the composition (C$_{II}$); and 2) a proportion of greater than or equal to 50 mol % and of less than or equal to 80 mol % of a composition (C$_{III}$).

10. The surfactant composition (C) according to claim 9, wherein:

1) said composition (C$_{II}$) comprises, per 100 mol %:

α) from 60 mol % to 80 mol % of the compound of formula (II),

β) from 15 mol % to 30 mol % of the compound of formula (II'), and

γ) up to 10 mol % of the compound of formula (II"), and 2) said composition (C$_{III}$) comprises, per 100 mol %:

α) from 60 mol % to 80 mol % of the compound of formula (III'), of its isomer of formula (IV) or of the mixture of these isomers, γ) from 15 mol % to 30 mol % of the compound of formula (III"), of its isomer of formula (IV") or of the mixture of these isomers, and γ) up to 10 mol % of the compound of formula (III"), of its isomer of formula (IV") or of the mixture of these isomers.

* * * * *